US011313795B1

(12) United States Patent
Yan et al.

(10) Patent No.: US 11,313,795 B1
(45) Date of Patent: Apr. 26, 2022

(54) BIOLOGICAL DETECTION DEVICE AND METHOD FOR TOILET WATER SOLUTION

(71) Applicant: Taiwan RedEye Biomedical Inc., Hsinchu (TW)

(72) Inventors: Shuo-Ting Yan, Hsinchu (TW); I-Hua Wang, Hsinchu (TW); Chen-Chung Chang, Hsinchu (TW); Tsung-Jui Lin, Hsinchu (TW)

(73) Assignee: Taiwan RedEye Biomedical Inc., Hsinchu (TW)

( * ) Notice: Subject to any disclaimer, the term of this patent is extended or adjusted under 35 U.S.C. 154(b) by 0 days.

(21) Appl. No.: 17/079,726

(22) Filed: Oct. 26, 2020

(51) Int. Cl.
*G01N 21/51* (2006.01)
*G01N 21/65* (2006.01)
*G01N 21/64* (2006.01)
*E03D 9/00* (2006.01)
*G01N 33/49* (2006.01)
*G01N 33/493* (2006.01)
*G01N 21/59* (2006.01)

(52) U.S. Cl.
CPC ............... *G01N 21/51* (2013.01); *E03D 9/00* (2013.01); *G01N 21/59* (2013.01); *G01N 21/6486* (2013.01); *G01N 21/65* (2013.01); *G01N 33/49* (2013.01); *G01N 33/493* (2013.01)

(58) Field of Classification Search
CPC .. A61B 10/0038; A61B 10/007; G01N 21/27; G01N 21/25; G01N 33/4833; E03D 11/13
See application file for complete search history.

(56) References Cited

U.S. PATENT DOCUMENTS

| | | | |
|---|---|---|---|
| 10,383,606 B1 * | 8/2019 | McCord | A61B 5/486 |
| 10,660,187 B1 * | 5/2020 | Zima | H05B 47/19 |
| 2018/0085098 A1 * | 3/2018 | Attar | G01N 33/493 |
| 2018/0184906 A1 * | 7/2018 | Prokopp | A61B 5/0022 |

* cited by examiner

*Primary Examiner* — Maurice C Smith

(57) ABSTRACT

A biological detection device for a toilet water solution includes a mounting portion, a main system, an adjustable support portion and a detection portion. The main system is connected to the mounting portion. The adjustable support portion can be adjusted for its movement in both horizontal and vertical directions and is connected to the mounting portion. The detection portion is connected and linked to the adjustable support portion and includes a light emitting source and an optical sensor. The biological detection device for a toilet water solution is a home healthcare device capable of automatically detecting whether there is blood in stool or urine without adding any chemical reagent or collecting any stool or urine specimen.

14 Claims, 16 Drawing Sheets

BIOLOGICAL DETECTION DEVICE AND METHOD FOR TOILET WATER SOLUTION

FIELD OF THE INVENTION

The present invention relates to a biological detection device and method, and more particularly to the biological detection device and method for a toilet water solution.

BACKGROUND OF THE INVENTION

The initial symptom of colorectal/rectal cancer is fecal occult blood, and the initial symptom of bladder cancer is urine occult blood, and both are related to occult blood. In the United States, the incidence of colorectal cancer accounts for 8% of the total incidence of cancers has a fourth rank in incidence rate and a second rank in mortality rate. In China, the incidence of colorectal cancer accounts 18.6% of the world, and the death toll accounts for 20.1% of the world, and both of the incidence and death toll ranks number one in the world. In Taiwan, the colorectal cancer is the top one of cancers in twelve consecutive years, and the incidence rate of colorectal cancer is the top one in the world. The journal "NATURE" presented in Nov. 9, 2017 that there was no universal screening method for bladder cancer. Only when people visually see blood in urine, they start knowing that there is a need for invasive endoscopic diagnosis and treatment, and approximately 10% of the patients having the symptom of blood in urine will be diagnosed with bladder cancer. It is feasible to use a non-invasive method for a urine test and can reduce the discomfort caused by the endoscopy.

A conventional immune occult blood test requires patients to collect a stool specimen by themselves, send the specimen to a hospital for testing, and wait for the test result. Such test is lack of immediate response and convenience. During the process of collecting the stool specimen, the occult blood in the stool is not uniformly distributed, occult blood may not be collected during the testing process to give a false negative result and cause a misjudgment. In some cases, a tumor or polyp bleeds intermittently, but not continuously, so that the tumor or polyp may not bleed on the same day or a day before collecting the stool specimen to give a false negative result and cause a misjudgment.

Japan Patent No. 1998339728 disclosed a stool composition examination device, wherein the device requires a stool collection step, a diluent addition step, and a washing step, and thus the use of such device is very inconvenient.

In addition, other conventional detection methods require adding chemicals that combine with the blood in the stool or urine, so that the additional step makes the test more inconvenient and the consumption of chemicals incurs a higher cost.

Therefore it is an important subject for related manufacturers to provide a device or method to meet the requirements of a quick and convenient biological detection while taking the cost and accuracy of the detection into consideration.

SUMMARY OF THE INVENTION

In view of the aforementioned drawbacks of the conventional detection method, the present invention provides a biological detection device for a toilet water solution to overcome the drawbacks of the prior art.

To achieve the aforementioned and other objectives, the present invention discloses a biological detection device for a toilet water solution, which is used for a biological detection, and the biological detection device comprises: a mounting portion, for mounting the biological detection device onto a toilet; a main system, including an operation control unit, and coupled to the mounting portion; an adjustable support portion, capable of being movably adjusted in a horizontal direction or a vertical direction, and coupled to the mounting portion; and a detection portion, placed in a toilet water solution containing an excrement, and comprising a light emitting source, and the detection portion being coupled and linked to the adjustable support portion, and the light emitting source being electrically coupled to the operation control unit; wherein, the operation control unit controls a light emitted from a light emitting source to pass through the toilet water solution containing the excrement and enter into an optical sensor which is electrically coupled to the operation control unit, and the optical sensor transmits a sensing signal to the operation control unit which is electrically coupled to the optical sensor, and the operation control unit determines whether or not there is a biological detection signal and outputs a detection result.

The present invention further discloses a biological detection method for a toilet water solution, provided for a biological detection, and applied to a biological detection device for a toilet water solution, and the device comprises a mounting portion, a main system, an adjustable support portion and a detection portion, and the device is mounted onto a toilet by the mounting portion, and the main system includes an operation control unit and is coupled to the mounting portion, and the adjustable support portion can be movably adjusted in a horizontal direction or a vertical direction and is coupled to the mounting portion, and the detection portion is placed into a toilet water solution containing an excrement and includes a light emitting source, and the detection portion is coupled and linked to the adjustable support portion, and the light emitting source is electrically coupled to the operation control unit. The biological detection method for a toilet water solution comprises the steps of: linking the adjustable support portion to the detection portion in a horizontal direction or a vertical direction; receiving a start detection instruction through an input unit; driving the light emitting source to shoot a light that passes through the toilet water solution containing the excrement and enters into an optical sensor; and determining whether or not there is a biological detection signal and sending a detection result to a display unit by the operation control unit.

The present invention can achieve the aforementioned objectives of the biological detection and meet the requirements for convenience, comfortability, quickness, accuracy and cost-effectiveness.

DESCRIPTION OF THE PREFERRED EMBODIMENTS

Figure 1:
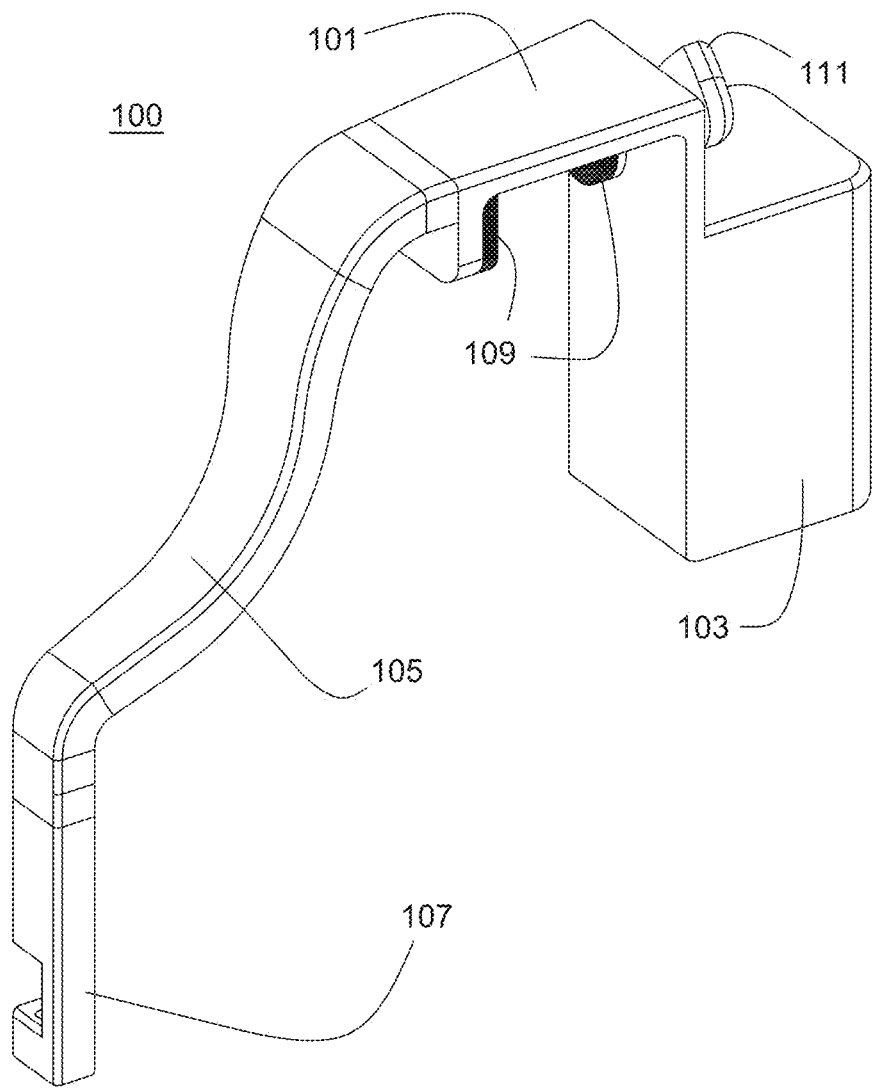
FIG. 1 is a perspective view of a biological detection device for a toilet water solution in accordance with a preferred embodiment of the present invention.
Figure 2:
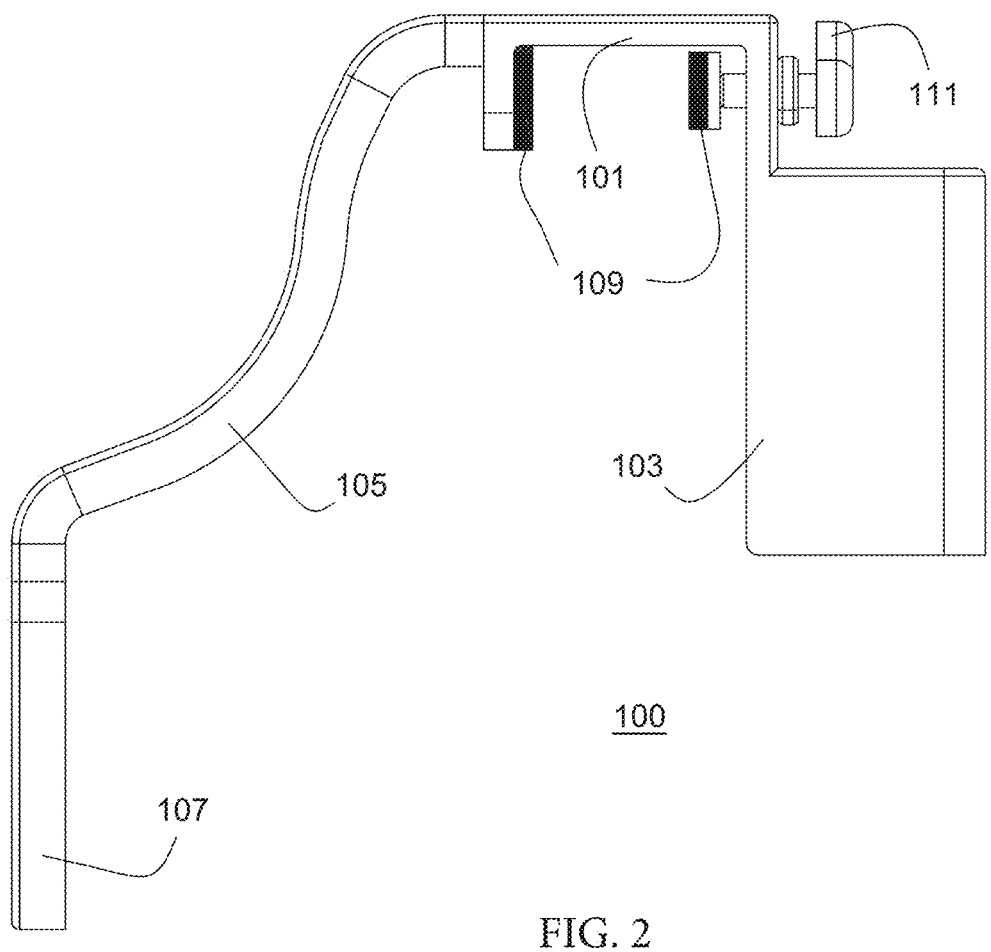
FIG. 2 is a side view of a biological detection device for a toilet water solution in accordance with a preferred embodiment of the present invention.

With reference to FIGS. 1 and 2 for the perspective view and side view of a biological detection device for a toilet water solution in accordance with a preferred embodiment of the present invention respectively, the biological detection device for a toilet water solution 100 comprises a mounting portion 101, a main system 103, an adjustable support portion 105 and a detection portion 107. The main system 103 is coupled to the mounting portion 101, and the adjustable support portion 105 includes a spiral tube that can be movably adjusted in three-dimensional directions and is coupled to the mounting portion 101. The detection portion 107 is coupled and linked to the adjustable support portion 105. The mounting portion 101 includes two opposite rubbers 109 and a screw 111, wherein the screw 111 is turned clockwise or counterclockwise to reduce the distance between the two opposite rubbers 109, so as to clamp a toilet and this method can be used to mount the biological detection device for a toilet water solution 100 onto the toilet.

In another embodiment of the present invention, the adjustable support portion comprises a spiral tube, a serrated structure, a telescopic sleeve, a universal shaft, a link rod and/or a keel structure that drives the adjustable support portion to move, twist, slide, displace and/or rotate within a specific range in an X-axis, Y-axis and/or Z-axis direction by an external force or an internal electromechanical control, so that the detection portion coupled to the adjustable support portion is submerged and fixed to an appropriate detection position in a toilet water solution. However, the structure of the adjustable support portion of the present invention is not limited to the aforementioned arrangement only, but numerous modifications and variations could be made thereto by those skilled in the art without departing from the scope and spirit of the invention.

Figure 3:
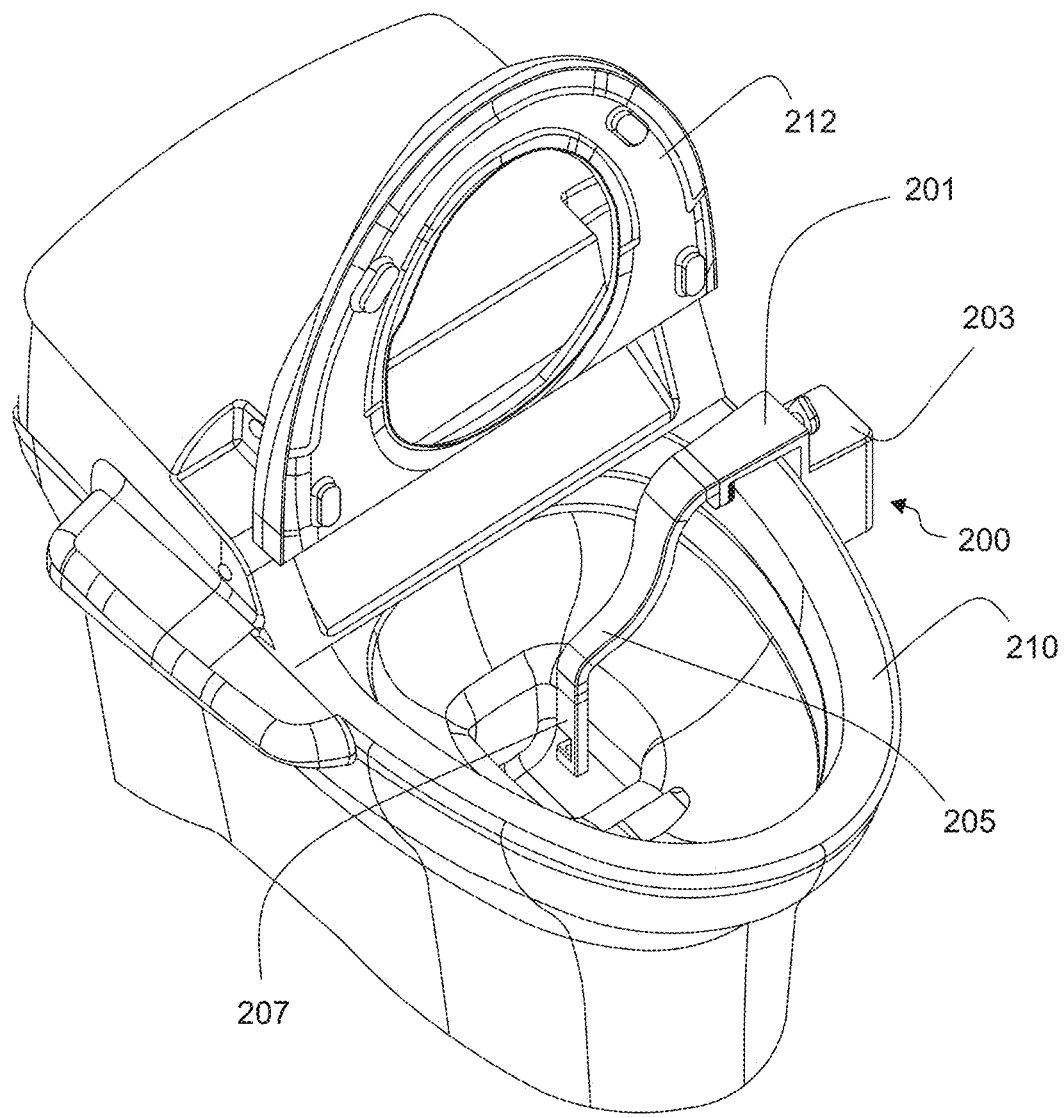
FIG. 3 is a first schematic view of a biological detection device for a toilet water solution installed to a toilet in accordance with a preferred embodiment of the present invention.
Figure 4:
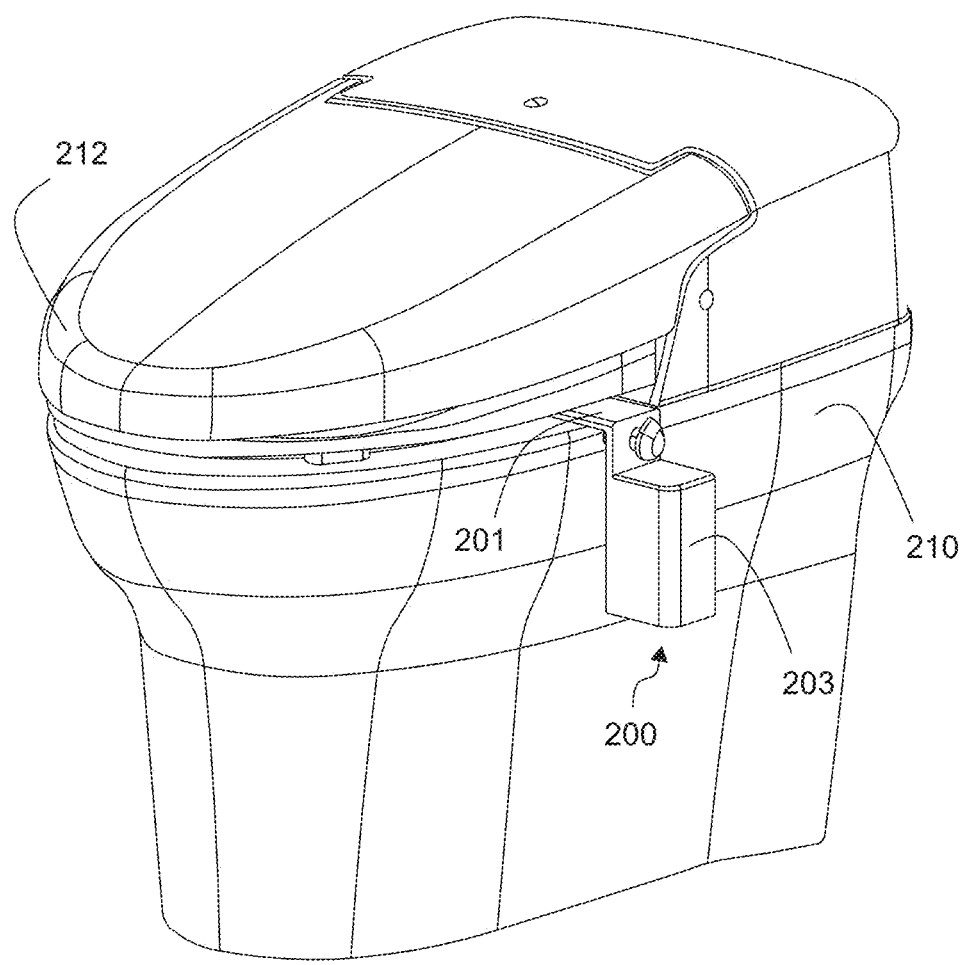
FIG. 4 is a second schematic view of a biological detection device for a toilet water solution installed to a toilet in accordance with a preferred embodiment of the present invention.

With reference to FIG. 3 for the first schematic view of a biological detection device for a toilet water solution in accordance with a preferred embodiment of the present invention, a toilet cover 212 of a toilet 210 is situated in a lift-open status. The biological detection device for a toilet water solution 200 comprises: a mounting portion 201, a main system 203, an adjustable support portion 205 and a detection portion 207. The mounting portion 201 is provided for mounting the biological detection device for a toilet water solution 200 onto the toilet 210. In this preferred embodiment, the biological detection device for a toilet water solution 200 is clamped onto the toilet 210 by the mounting portion 201. The adjustable support portion 205 can be moved in three-dimensional directions and linked to the detection portion 207. The detection portion 207 is placed into a toilet water solution (not shown in the figure) containing an excrement (such as urine and/or stool) in the toilet 210, and the detection portion 207 is linked by the adjustable support portion 205 and can be adjusted and fixed to an appropriate detection position in the toilet water solution containing the excrement in the toilet 210. With reference to FIG. 4 for the second schematic view of a biological detection device for a toilet water solution in accordance with a preferred embodiment of the present invention, the biological detection device 200 is mounted onto the toilet 210, and the toilet cover 212 of the toilet 210 is situated in a closed status. The biological detection device for a toilet water solution 200 is mounted onto the toilet 210 by the mounting portion 201, and when the toilet cover 212 is closed onto the toilet 210, the main system 203 is exposed from the toilet 210 to facilitate users to operate the functions of the main system and view the displayed messages.

In another embodiment of the present invention, the biological detection device for a toilet water solution can be mounted, fixed, or installed on a toilet (or a toilet cover) or to a side of the toilet (or the toilet cover) by using the mounting portion by a clamping, suspending, sucking, pasting, binding, socketing, latching buckling, magnetically attracting, riveting, screwing, or locking method, and the structure of the mounting portion corresponding to the aforementioned method includes but not limited to a clamp, an adhesive, a strap, a screw, a nut, a snap, a magnet, a rivet or a sucking disc, etc. However, the present invention is not limited to the aforementioned arrangement only, but numerous modifications and variations could be made thereto by those skilled in the art without departing from the scope and spirit of the invention.

Figure 5:
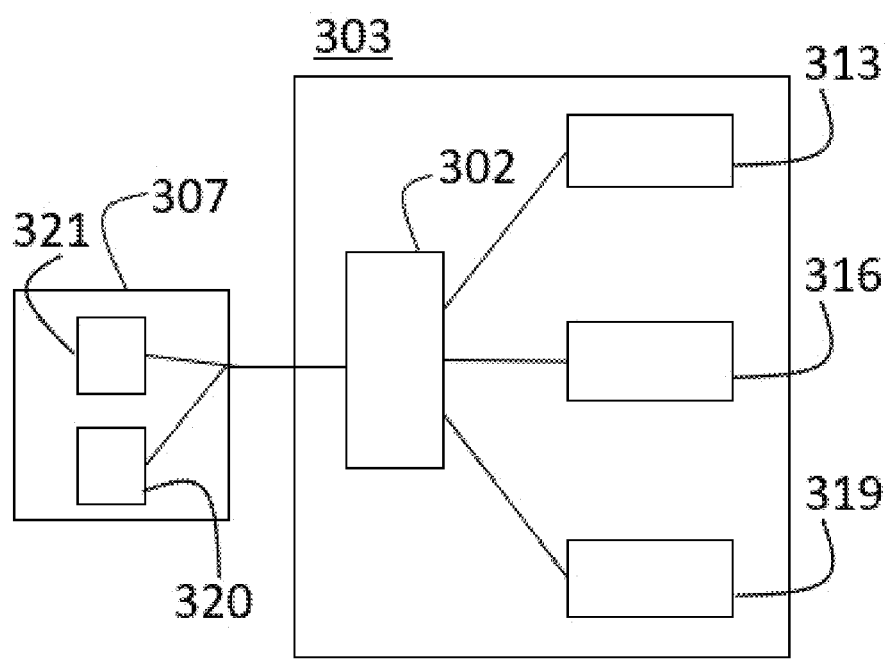
FIG. 5 is a block diagram of a biological detection method for a toilet water solution in accordance with a preferred embodiment of the present invention

With reference to FIG. 5 for a block diagram of the biological detection device for a toilet water solution in accordance with a preferred embodiment of the present invention, the main system 303 comprises an operation control unit 302, an input unit 313, a display unit 316 and a power supply 319. The detection portion 307 comprises a light emitting source 321 and an optical sensor 320. The operation control unit 302 is electrically coupled to the input unit 313, the display unit 316, and the power supply 319, and the operation control unit 302 is electrically coupled to the light emitting source 321 and the optical sensor 320 of the detection portion 307.

In the present invention, the operation control unit such as a MCU or a CPU is a unit with operating, processing, controlling and/or analyzing functions. The power supply can be a battery (either a replaceable or rechargeable battery) or an external alternate current, and when the power supply is the external alternate current, then the power supply includes a DC/AC conversion circuit. The input unit can be a physical button, a voice control module, or an LCD touch display device for receiving a detection instruction or an instruction of controlling the adjustable support portion. When the input unit is the LCD touch display device, the input unit includes a user interface. The input unit comes with different options for different detection objects (such as blood, uric acid, urine protein and urine sugar). The display unit can be an LCD touch display device or an LED lamp for displaying detection results and information. The light emitting source can be an LED lamp or a laser and has a controller, and the light emitting source can shoot out light beams of different wavelengths. The optical sensor can be a spectrophotometer, a photodiode, a CMOS sensor or a CCD sensor with a controller. However, the present invention is not limited to the aforementioned arrangements.

In another embodiment, the main system is combined with an (external) washlet, or the power of the main system can even be supplied by the washlet. Further, the main system can be integrated with the washlet to share the operation control unit, the input unit, the display unit, and the power supply The biological detection device for a toilet water solution of the present invention is used for a biological detection. In the following preferred embodiment of the present invention, the biological detection of blood is used as an example for illustrating the invention, and the biological detection of other embodiments can be a biological detection of uric acid, urine protein or urine sugar. In different embodiments, the principle of the biological detection includes but not limited to the detection based on absorption, fluorescence, scattering, or Raman spectrum property.

Figure 6:
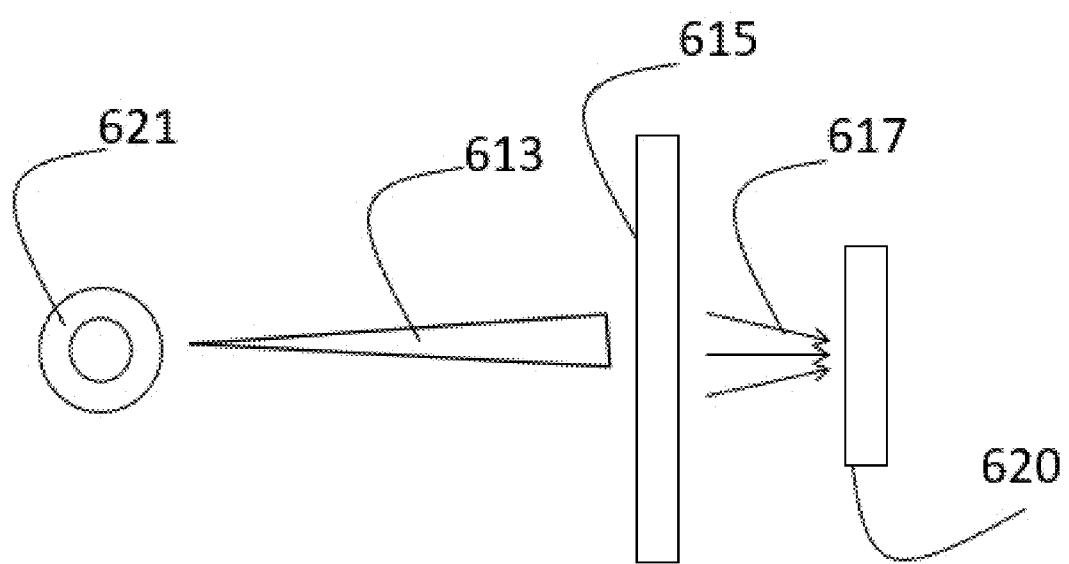
FIG. 6 is a schematic view showing the principle of a biological detection for a toilet water solution of the present invention.

With reference to FIG. 6 for a schematic view showing the principle of a biological detection for a toilet water solution of the present invention, the operation control unit controls the light emitting source 621 to shoot out a light beam 613 with a specific wavelength (such as 250-650 nm), and the light beam 613 enters and passes through the toilet water solution containing an excrement 615 (or an object to be tested) and becomes a penetrating light 617 that enters into the optical sensor 620, and a sensing signal is generated after the optical sensor 620 receives the penetrating light 617, and the sensing signal is transmitted to the operation control unit.

Figure 7:
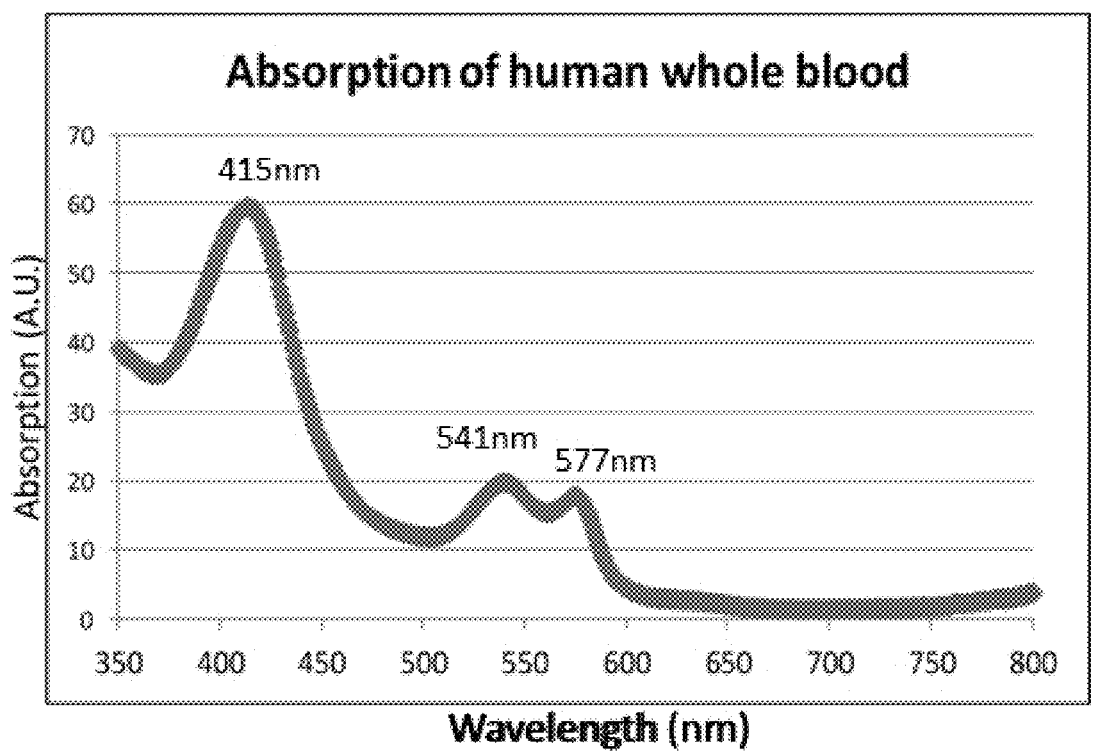
FIG. 7 is a graph of a blood absorption spectrum of a preferred embodiment of the present invention.

With reference to FIG. 7 for a blood absorption spectrum of a preferred embodiment of the present invention, the operation control unit receives the sensing signal and then determines whether or not there is a biological detection signal (which is an occult blood signal in this embodiment), and if it is determined that the sensing signal has a characteristic absorption peak value of 415 nm, 541 nm or 577 nm as shown in FIG. 7, then it will be decided that there is an occult blood (heme) signal. The operation control unit outputs a detection result (containing the occult blood signal) to a display unit and controls the display unit to display the detection result. In another embodiment, the operation control unit controls the light source to emits a light beam with a different wavelength according to the object of the biological detection (such as uric acid, urine protein or urine sugar), and the spectral determination method varies (according to clinical trial results and statistics of data.

The foregoing preferred embodiment mainly uses the biophysics of blood to perform the detection. Besides detecting a trace amount of blood, the biological detection device for a toilet water solution in accordance with the present invention can also adopt the biological detection of uric acid, urine protein, or urine sugar, etc.

Figure 8:
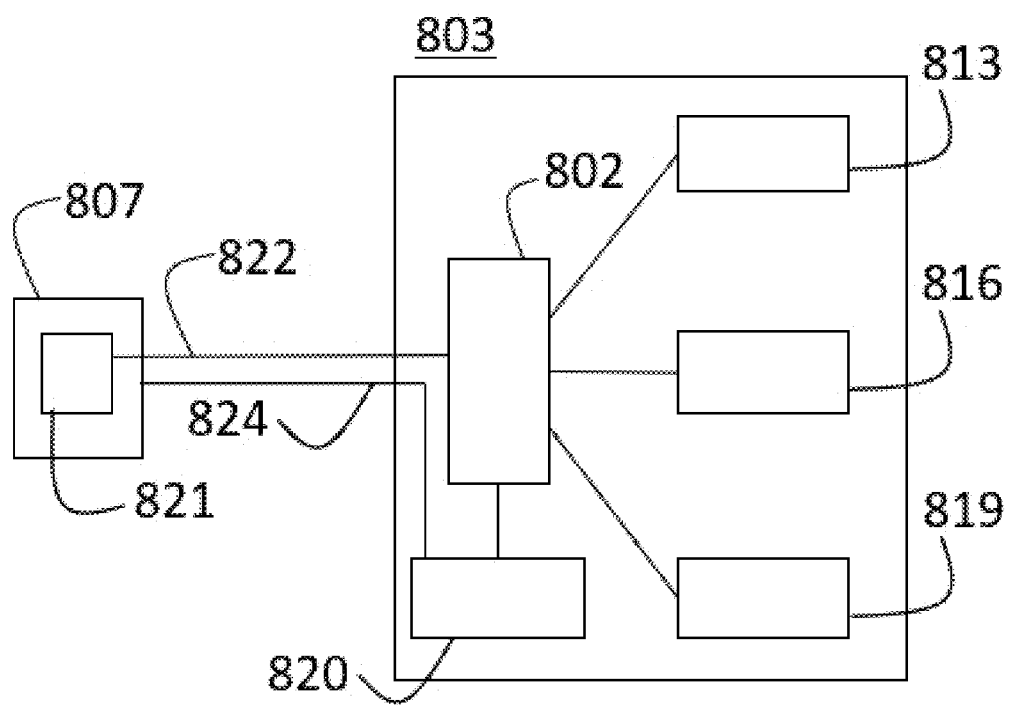
FIG. 8 is a block diagram of a biological detection device for a toilet water solution in accordance with a first embodiment of the present invention.
Figure 9:
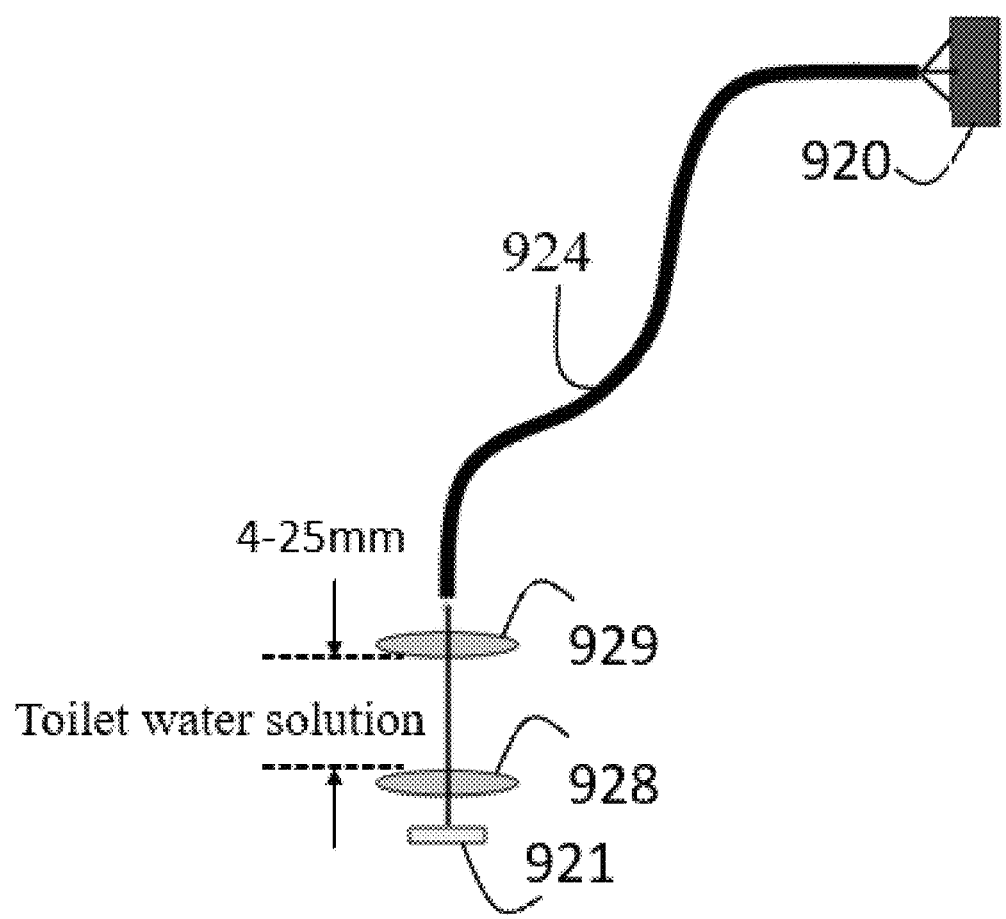
FIG. 9 is a schematic view of a light transmission in accordance with the first embodiment of the present invention.

With reference to FIG. 8 for the block diagram of a biological detection device for a toilet water solution in accordance with the first embodiment of the present invention, only the difference between the biological detection devices of the first embodiment and the preferred embodiment will be described below and their same technical characteristics will not be repeated. The difference between the first embodiment and the preferred embodiment resides on that the main system 803 of the first embodiment comprises an operation control unit 802, an input unit 813, a display unit 816, a power supply 819 and an optical sensor 820, and the detection portion 807 comprises a light emitting source 821. The light emitting source 821 is electrically coupled to the operation control unit 802 through an electroconductive tube 822, and the light emitting source 821 and the optical sensor 820 transmit light beams to each other through a photoconductive tube 824 (including but not limited to an optical fiber). With reference to FIG. 9 for a schematic view of a light transmission of the first embodiment of the present invention, the operation control unit controls a light emitting source 921 to shoot out a light beam that passes through the toilet water solution containing the excrement through a planar transparent glass 928 and becomes a penetrating light, and the penetrating light enters into a photoconductive tube 924 through a transparent glass 929 and passes through the photoconductive tube 924 to reach the optical sensor 920. The two pieces of transparent glass 928, 929 are arranged in the toilet water solution, and the distance between the two pieces of transparent glass 928, 929 is approximately equal to 4-25 mm.

Figure 10:
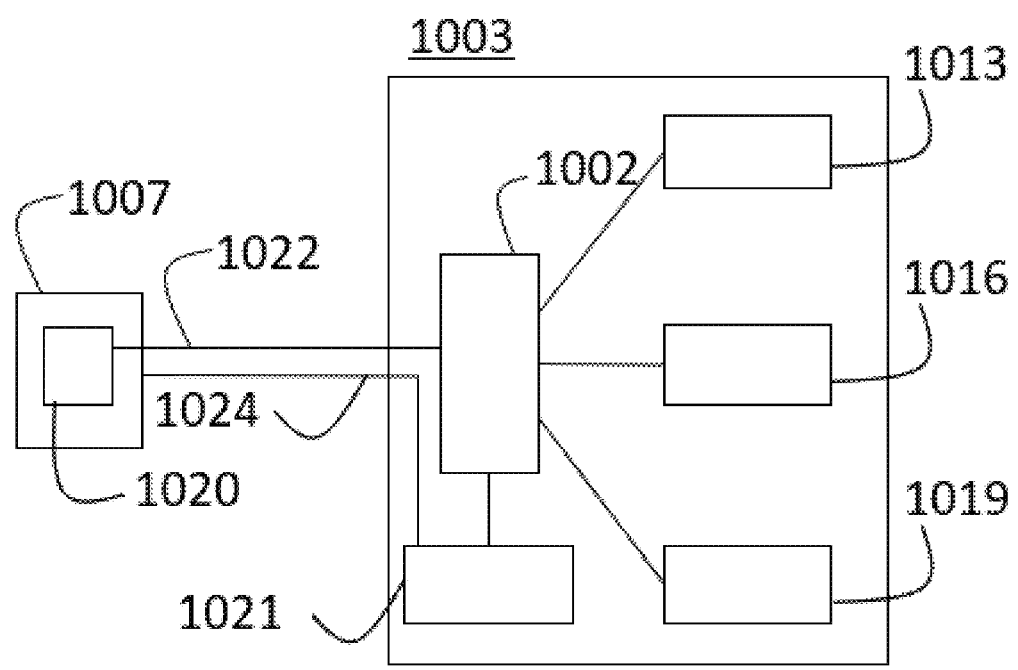
FIG. 10 is a block diagram of a biological detection device for a toilet water solution in accordance with a second embodiment of the present invention.
Figure 11:
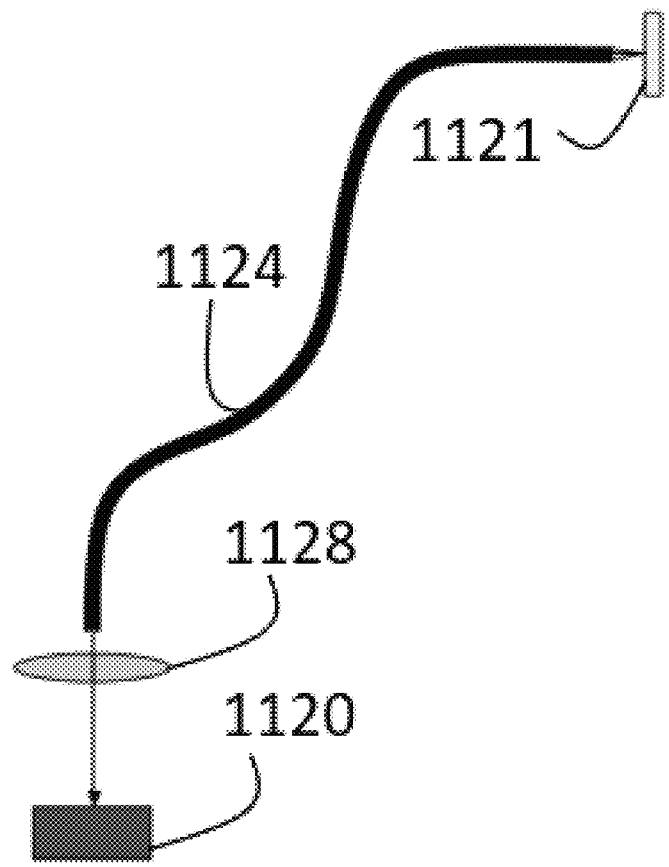
FIG. 11 is a schematic view of a light transmission in accordance with the second embodiment of the present invention.

With reference to FIG. 10 for the block diagram of a biological detection device for a toilet water solution in accordance with the second embodiment of the present invention, only the difference between the biological detection devices of the first embodiment and the preferred embodiment will be described below and their same technical characteristics will not be repeated. The difference between the second embodiment and the preferred embodiment resides on that a main system 1003 of the second embodiment comprises an operation control unit 1002, an input unit 1013, a display unit 1016, a power supply 1019 and a light emitting source 1021, and a detection portion 1007 comprises an optical sensor 1020. The optical sensor 1020 is electrically coupled to the operation control unit 1002 through an electroconductive tube 1022, and the light emitting source 1021 and the optical sensor 1020 transmit light beams to each other through a photoconductive tube 1024. With reference to FIG. 11 for a light transmission in accordance with the second embodiment of the present invention, the operation control unit controls a light emitting source 1121 to shoot a light beam through toilet water solution containing an excrement through a photoconductive tube 1124 and a planar transparent glass 1128 and becomes a penetrating light, and the penetrating light enters into an optical sensor 1120.

Figure 12:
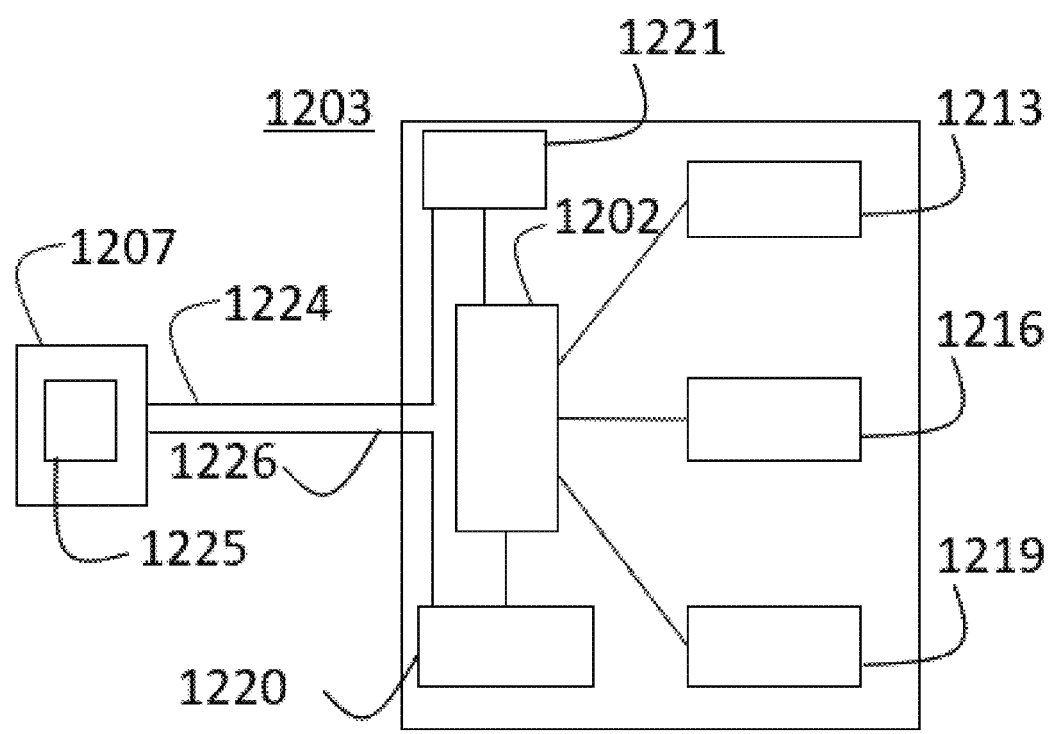
FIG. 12 is a block diagram of a biological detection device for a toilet water solution in accordance with a third embodiment of the present invention.

With reference to FIG. 12 for the block diagram of a biological detection device for a toilet water solution in accordance with the third embodiment of the present invention, only the difference between the biological detection devices of the third embodiment and the preferred embodiment will be described below and their same technical characteristics will not be repeated. The difference between the third embodiment and the preferred embodiment resides on that a main system 1203 of the third embodiment comprises an operation control unit 1202, an input unit

Figure 13:
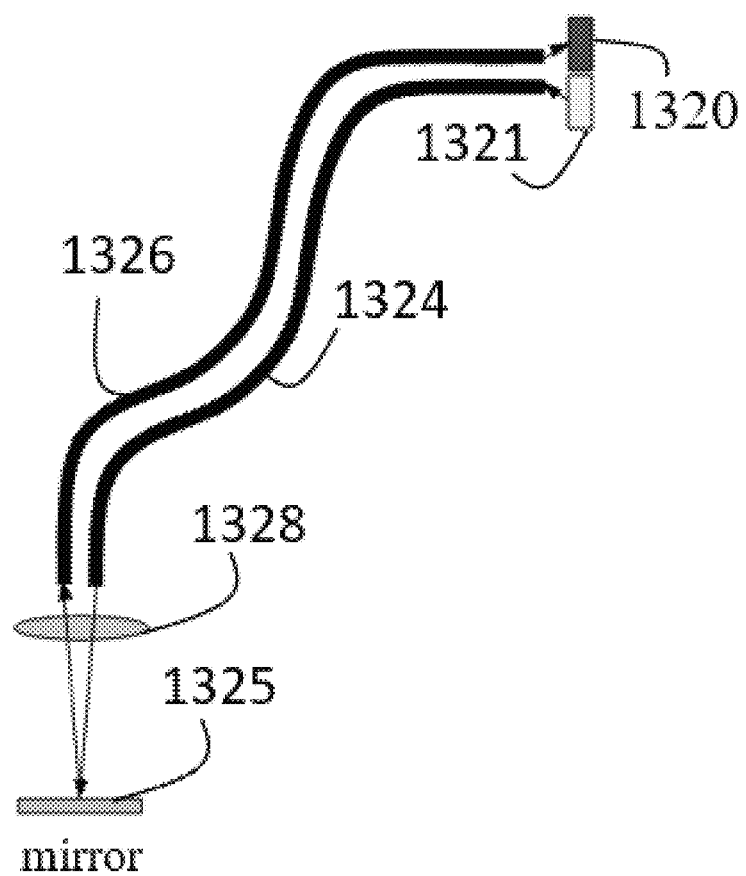
FIG. 13 is a schematic view of a light transmission in accordance with the third embodiment of the present invention.

1213, a display unit 1216, a power supply 1219, an optical sensor 1220 and a light emitting source 1221, and the optical sensor 1220 and the light emitting source 1221 are electrically coupled to the operation control unit 1202. The detection portion 1207 comprises a mirror 1225. The light emitting source 1221 and the optical sensor 1220 transmit light beams to each other through a photoconductive tube 1224 and a photoconductive tube 1226. With reference to FIG. 13 for the schematic view of a light transmission in accordance with the third embodiment of the present invention, the operation control unit controls a light emitting source 1321 to shoot a light beam that passes through toilet water solution containing an excrement through a photoconductive tube 1324 and a transparent glass 1328 and becomes a penetrating light, and the penetrating light is returned to the transparent glass 1328 and the photoconductive tube 1326 by the reflection of the mirror 1325 and transmitted to an optical sensor 1320.

Figure 14:
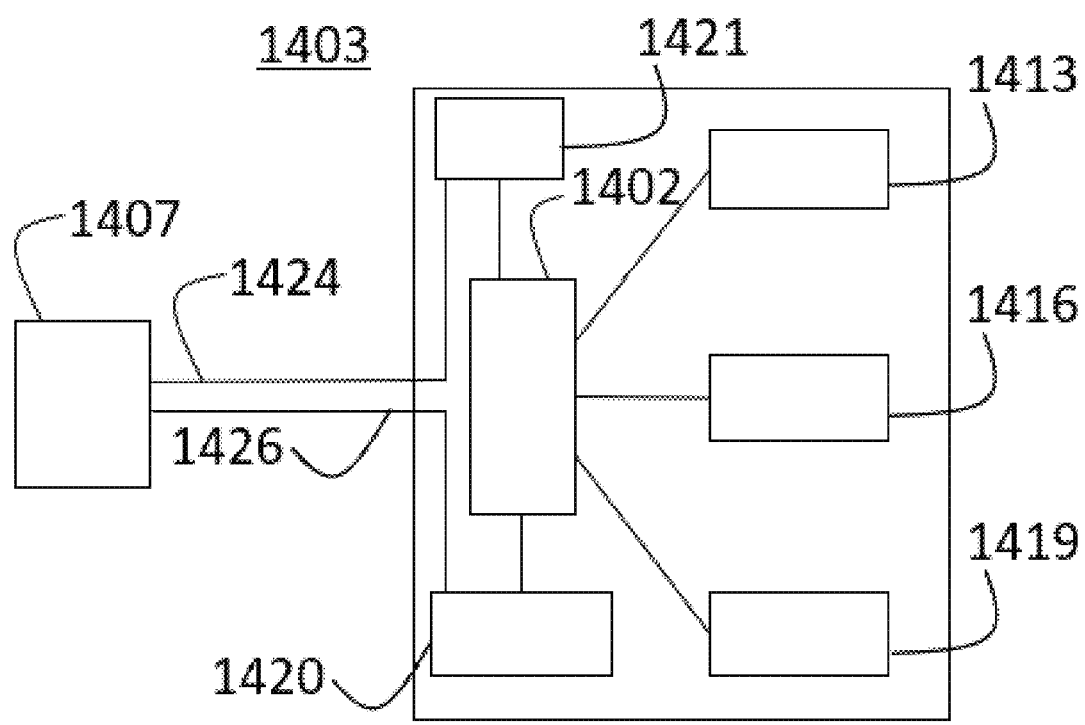
FIG. 14 is a block diagram of a biological detection device for a toilet water solution in accordance with a fourth embodiment of the present invention.
Figure 15:
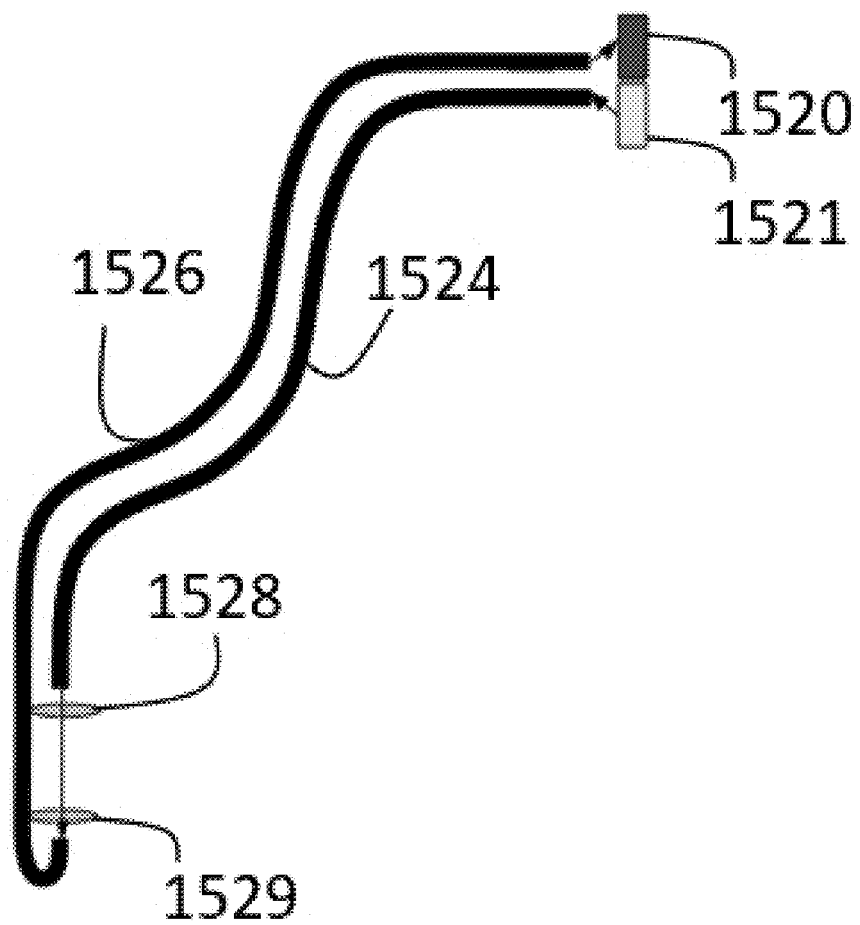
FIG. 15 is a schematic view of a light transmission in accordance with the fourth embodiment of the present invention.

With reference to FIG. 14 for the block diagram of a biological detection device for a toilet water solution in accordance with the fourth embodiment of the present invention, only the difference between the biological detection devices of the fourth embodiment and the preferred embodiment will be described below and their same technical characteristics will not be repeated. The difference between the fourth embodiment and the preferred embodiment resides on that a main system 1403 of the fourth embodiment comprises an operation control unit 1402, an input unit 1413, a display unit 1416, a power supply 1419, an optical sensor 1420 and a light emitting source 1421, and the detection portion 1407 is placed into a toilet water solution and coupled to a photoconductive tube 1424 and a photoconductive tube 1426, so that a light beam transmitted by the photoconductive tube 1424 can be transmitted to the photoconductive tube 1426. An end of the photoconductive tube 1424 and an end of photoconductive tube 1426 are placed into a toilet water solution, and an end of the photoconductive tube 1424 is configured to be corresponsive to an end of the photoconductive tube 1426, so that the light beam transmitted from an end of the photoconductive tube 1424 can be passed through the toilet water solution and transmitted to an end of the photoconductive tube 1426. Both of the light transmission by the light emitting source 1421 and the light reception by the optical sensor 1420 use the photoconductive tube, and such arrangement is different from the third embodiment and does not use a mirror to change the light path direction. Light beam is transmitted between the light emitting source 1421 and the optical sensor 1420 by the photoconductive tube 1424 and the photoconductive tube 1426. With reference to FIG. 15 for the schematic view of a light transmission in accordance with the fourth embodiment of the present invention, the operation control unit controls a light emitting source 1521 to shoot out a light beam that passes through a toilet water solution containing an excrement through a photoconductive tube 1524 and a transparent glass 1528 and becomes a penetrating light, and the penetrating light is transmitted to the optical sensor 1520 through the transparent glass 1529 and the photoconductive tube 1526.

Figure 16:
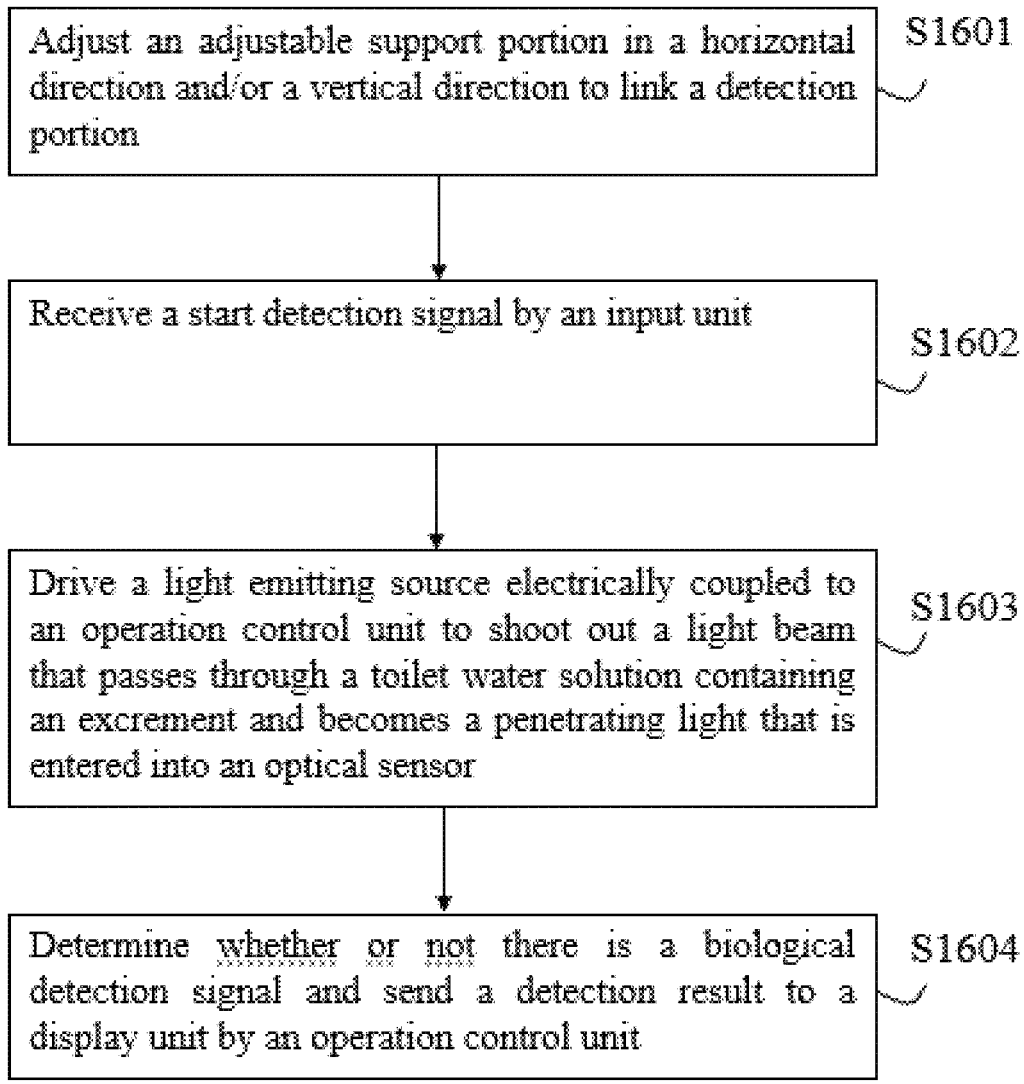
FIG. 16 is a flow chart of a biological detection method for a toilet water solution in accordance with an exemplary embodiment of the present invention.

With reference to FIG. 16 for the flow chart of a biological detection method for a toilet water solution in accordance with an exemplary embodiment of the present invention, the present invention provides a biological detection method for a toilet water solution to perform a biological detection, this exemplary embodiment uses the biological detection of blood as an example to illustrate the present invention, and the biological detection is other embodiments includes a biological detection of uric acid, urine protein or urine sugar, etc. The principle of the biological detection of other embodiments includes but not limited to the use of absorption, fluorescence, scattering, or Raman spectrum property.

The biological detection method for a toilet water solution in accordance with the present invention is applied to a biological detection device for a toilet water solution, wherein the related content of the biological detection device for a toilet water solution in accordance with the preferred embodiment and the first to fourth embodiments of the present invention have been described above and illustrated by FIGS. 1 to 5 and 8 to 15. The biological detection device for a toilet water solution comprises a mounting portion, a main system, an adjustable support portion and a detection portion. The biological detection device for a toilet water solution is mounted onto a toilet by the mounting portion. The adjustable support portion can be moved in three-dimensional directions and linked to the detection portion. The detection portion is placed into a toilet water containing an excrement (such as urine and/or stool) in the toilet and linked by the adjustable support portion, so that the detection portion can be adjusted and fixed to an appropriate detection position in the toilet water solution containing the excrement in the toilet. The main system comprises an operation control unit, a display unit, an input unit and a power supply coupled to the mounting portion. The light emitting source and the optical sensor is electrically coupled to the operation control unit.

The biological detection method for a toilet water solution in accordance with an embodiment of the present invention comprises the following steps S1601 to S1604:

S1601: An adjustable support portion is adjusted to link a detection portion in a horizontal direction and/or a vertical direction. The adjustable support portion is adjusted by an external force or an internal electromechanical control to move, twist, slide, displace and/or rotate in an X-axis, Y-axis and/or Z-axis direction, so that the adjustable support portion coupled and linked to the detection portion can be submerged and then fixed to an appropriate detection position in the toilet water solution.

S1602: An input unit receives a start detection instruction, wherein the input unit receives the start detection instruction inputted by users to start performing detection. The input unit such as a physical button, a voice control module or an LCD touch display device is provided for the users to input the start detection instruction or an instruction for controlling the adjustable support portion to make adjustments. When the input unit is the LCD touch display device, the input unit includes a user interface. The input unit has options for different detection objects (such as blood, uric acid, urine protein and urine sugar). It is noteworthy that the sequence of the aforementioned steps S1601 and S1602 is not restricted.

S1603: The light emitting source electrically coupled to an operation control unit is driven to shoot out a light beam that passes through a toilet water solution containing an excrement and becomes a penetrating light, and the penetrating light enters into an optical sensor, and the optical sensor generates a corresponding sensing signal, and the operation control unit receives the sensing signal transmitted from the optical sensor. With reference to FIG. 6 and the related content of FIG. 6 as described above, the input unit receives the start detection instruction and then generates the start signal, so that the operation control unit controls the light emitting source 621 to shoot out a light beam 613 with a specific wavelength (such as 250-650 nm), and the light beam 613 is shot and passed through the toilet water solution containing an excrement 615 (or an object to be tested) to become a penetrating light 617, and the penetrating light 617 enters into the optical sensor 620, and the optical sensor 620 receives the penetrating light 617 to generate the corresponding sensing signal and transmits the sensing signal to the operation control unit.

S1604: The operation control unit determines whether or not there is a biological detection signal and sends a detection result to a display unit.

With reference to FIG. 7 and the content related to FIG. 7, the operation control unit receives a sensing signal and then determines whether or not there is a biological detection signal (such as an occult blood signal in this embodiment), and if it is determined that the sensing signal has a characteristic peak value of approximately 415 nm, 541 nm, or 577 nm as shown in FIG. 7, then it will be decided that there is an occult blood (heme) signal. The operation control unit outputs a detection result (containing the occult blood signal) to a display unit and controls the display unit to display the detection result. In another embodiment, the operation control unit controls the light source to emits a light beam with a different wavelength according to the object of the biological detection (such as uric acid, urine protein or urine sugar), and the spectral determination method varies (according to clinical trial results and statistics of data.

In addition, the biological detection device for a toilet water solution is mounted, fixed, or installed on the toilet by the mounting portion by a clamping, suspending, sucking, pasting, binding, socketing, latching, buckling, magnetic attracting, riveting, screwing, or locking method, and the structure of the mounting portion corresponding to the aforementioned methods includes a clamp, an adhesive, a strap, a screw, a nut, a snap, a magnet, a rivet or a sucking disc.

In another embodiment, the adjustable support portion comprises a spiral tube, a serrated structure, a telescopic sleeve, a universal shaft, a link rod or a keel structure that drives the adjustable support portion to move, twist, slide, displace and/or rotate within a specific range in an X-axis, Y-axis and/or Z-axis direction by an external force or an internal electromechanical control, so that the detection portion coupled to the adjustable support portion is submerged and fixed to an appropriate detection position in a toilet water solution.

In another embodiment, the main system can be combined with an (external) washlet, or the power of the main system can even be supplied by the washlet. Further, the main system can be integrated with the washlet to share the operation control unit, the input unit, the display unit, and the power supply.

The basic detection principle of the aforementioned embodiment of the present invention is based on the measurement of blood absorption spectrum, but the detection principle should be limited to blood absorption only, and any property of fluorescence, scattering, or Raman spectrum used for measuring the general blood spectrum can be used as a basis for detecting whether or not there is a trace of blood in the toilet water solution containing the excrement.

In summation, the present invention provides a biological detection device for a toilet water solution (which is a home healthcare device) and a biological detection method for a toilet water solution capable of automatically detecting whether or not there is blood, uric acid, urine protein or urine sugar in the excrement without requiring any biological/chemical agents, diluents, or test paper, or the collection of any stool or urine specimen, or any stool or urine collection procedure, and thus the invention is suitable for home operation by ordinary people. Using a non-invasive method to detect whether the excrement is abnormal can reduce the discomfort caused by traditional endoscopic examination and achieve the purpose of the biological detection of the present invention.

While the invention has been described by means of specific embodiments, numerous modifications and variations could be made thereto by those skilled in the art without departing from the scope and spirit of the invention as set forth in the claims.

What is claimed is:

1. A biological detection device, comprising:
   an adjustable supporting arm;
   a lighting element, being disposed on a first end of the adjustable supporting arm;
   a mounting device, being connected to a second end of the adjustable supporting arm, and being adopted to be connected to a bowl of a toilet, such that the adjustable supporting arm is therefore positioned over the bowl, and the lighting element being positioned in the bowl; and
   an electronic device, being disposed to be near to one side of the bowl by being connected to the mounting device, and comprising a light sensor and a processor;
   wherein the processor is coupled to the lighting element and the light sensor, and comprising at least one embedded program including instructions for:
   controlling the lighting element to emit a detection light to pass through an excrement and/or a urine existing in a toilet water solution contained by the bowl of the toilet;
   controlling the light sensor to collect a transmitted light of the detection light from the excrement and/or the urine via a photoconductive tube; and
   conducting a biological analysis by applying at least one signal process to an electric signal that is received from the light sensor, thereby generating at least one biological data.

2. The biological detection device for a toilet water solution as claimed in claim 1, wherein the electronic device further comprises an input/output interface and a display coupled to the processor.

3. The biological detection device as claimed in claim 1, wherein the processor is coupled to the lighting element through an electroconductive tube.

4. The biological detection device as claimed in claim 1, wherein the biological data comprises level of blood, level of uric acid, level of urine protein, and/or level of urine sugar.

5. The biological detection device as claimed in claim 1, wherein the mounting device is connected to the bowl by a way of clamping, suspending, sucking, pasting, binding, socketing, latching, buckling, magnetic attracting, riveting, screwing, or locking.

6. The biological detection device as claimed in claim 1, wherein the adjustable supporting arm comprises spiral tube, a serrated structure, a telescopic sleeve, a universal shaft, a link rod, or a keel structure.

7. The biological detection device as claimed in claim 1, wherein the electronic device is combined with a washlet.

8. A biological detection method, being conducted by a biological detection device that comprises an adjustable supporting arm, a lighting element disposed on a first end of the adjustable supporting arm, a mounting device connected to a second end of the adjustable supporting arm, and an electronic device that is connected to the mounting device and comprises a light sensor and a processor coupled to the light sensor and the lighting element the biological detection method comprising the steps of:

(1) disposing the adjustable supporting arm over a bowl of a toilet by connecting the mounting device to the bowl, thereby making the first end of the adjustable supporting arm be positioned in the bowl; and (2) transmitting a start instruction to the processor, such that the processor controls the lighting element to emit a detection light to pass through an excrement and/or a urine existing in a toilet water solution contained by the bowl of the toilet, subsequently controlling the light sensor to collect a transmitted light of the detection light from the excrement and/or the urine via a photoconductive tube, and eventually conducting a biological analysis by applying at least one signal process to an electric signal that is received from the light sensor, thereby generating at least one biological data.

9. The biological detection method as claimed in claim 8, wherein the electronic device further comprises an input/output interface and a display coupled to the processor.

10. The biological detection method as claimed in claim 8, wherein the processor is coupled to the lighting element through an electroconductive tube.

11. The biological detection method as claimed in claim 8, wherein the biological data comprises level of blood, level of uric acid, level of urine protein, and/or level of urine sugar.

12. The biological detection method as claimed in claim 8, wherein the mounting device is connected to the bowl by a way of clamping, suspending, sucking, pasting, binding, socketing, latching, buckling, magnetic attracting, riveting, screwing, or locking.

13. The biological detection method as claimed in claim 8, wherein the adjustable supporting arm comprises spiral tube, a serrated structure, a telescopic sleeve, a universal shaft, a link rod, or a keel structure.

14. The biological detection method as claimed in claim 8, wherein the electronic device is combined with a washlet.

* * * * *